(12) United States Patent
Hunt

(10) Patent No.: US 8,137,677 B2
(45) Date of Patent: Mar. 20, 2012

(54) NON-PROTEIN STABILIZED CLOSTRIDIAL TOXIN PHARMACEUTICAL COMPOSITIONS

(75) Inventor: Terrence J. Hunt, Corona, CA (US)

(73) Assignee: Allergan, Inc., Irvine, CA (US)

( * ) Notice: Subject to any disclaimer, the term of this patent is extended or adjusted under 35 U.S.C. 154(b) by 977 days.

(21) Appl. No.: 11/524,683

(22) Filed: Sep. 21, 2006

(65) Prior Publication Data

US 2010/0279953 A1 Nov. 4, 2010

Related U.S. Application Data

(60) Provisional application No. 60/725,426, filed on Oct. 6, 2005.

(51) Int. Cl.
*A61K 39/02* (2006.01)
*A61K 39/00* (2006.01)
*A61K 39/08* (2006.01)
(52) U.S. Cl. ............... 424/234.1; 424/184.1; 424/236.1; 424/247.1
(58) Field of Classification Search ........................ None
See application file for complete search history.

(56) References Cited

U.S. PATENT DOCUMENTS

| | | | | |
|---|---|---|---|---|
| 5,512,547 | A | 4/1996 | Johnson et al. | 514/21 |
| 5,696,077 | A | 12/1997 | Johnson et al. | 514/2 |
| 5,756,468 | A | 5/1998 | Johnson et al. | 514/21 |
| 6,087,327 | A | 7/2000 | Pearce et al. | 514/2 |
| 2003/0118598 | A1 | 6/2003 | Hunt | 424/184.1 |

FOREIGN PATENT DOCUMENTS

| | | |
|---|---|---|
| CN | 1 215 084 | 4/1999 |
| EP | 1 112 082 B1 | 7/2002 |
| EP | 1 253 932 B1 | 4/2005 |
| WO | WO 01/93827 A | 12/2001 |
| WO | WO 2004/060384 A | 7/2004 |
| WO | WO 2006/020208 A | 2/2006 |

OTHER PUBLICATIONS

Parish et al (Clinics in Dermatology, 2003:21:481-484).*
Nizai, (Handbook of Pharmaceutical Manufacturing Formulations Liquid Products, vol. 3, 2004, p. 58).*
Goodnough et al (Applied and Environmental Microbiology, Oct. 1992, vol. 58, No. 10, p. 3426-3428).*
Carpenter (Formulation and Delivery of Protein and Peptides, vol. 567, p. 134-147).*
Panicker et al (Neurology India, Oct.-Dec. 2003, vol. 51, Issue 4, p. 455-460).*
Carpenter et al., *Interactions of Stabilizing Additives with Proteins During Freeze-Thawing and Freeze-Drying*, International Symposium on Biological Product Freeze-Drying and Formulation, Oct. 24-26, 1990; Karger (1992), 225-239.
Goodnough M.C., et al., *Recovery of type-A botulinal toxin following lyophilization*, Acs Symposium Series 1994;567(–):193-203.
Goodnough M.C., et al., *Stabilization of Botulinum Toxin Type A During Lyophilization*, App & Envir. Micro. 58 (10) 3426-3428 (1992).
Kohl A., et al., *Comparison of the effect of botulinum toxin A (Botox (R)) with the highly-purified neurotoxin (NT 201) in the extensor digitorum brevis muscle test*, Mov Disord 2000;15(Suppl 3):165.
Naumann et al., *Botulinum toxin type A in the treatment of focal, axillary, and palmar hyperhidrosis and other hyperhidrotic conditions*, European J. Neurology 6 (Supp 4): S111-S115:1999.
Ragona, et al., *Management of Parotid Sialocele with BotulinumToxin*, The Laryngoscope 109:1344-1346:1999.
Schantz E.J., et al., Preparation and characterization of botulinum toxin type A for human treatment, chapter 3 of Jankovic, J., et al, *Therapy with Botulinum Toxin*, Marcel Dekker, Inc (1994).
Schantz E.J., et al., *Properties and use of botulinum toxin and other microbial neurotoxins in medicine*, Microbiol Rev Mar. 1992;56(1):80-99.
Singh, *Critical Aspects of Bacterial Protein Toxins*, pp. 63-84 (chapter 4) of Natural Toxins II, edited by B.R. Singh et al., Plenum Press, New York (1976).

* cited by examiner

*Primary Examiner* — Vanessa L. Ford
(74) *Attorney, Agent, or Firm* — Hal Gibson; Debra Condino

(57) ABSTRACT

A Clostridial toxin pharmaceutical composition comprising a Clostridial toxin, such as a botulinum toxin, wherein the Clostridial toxin present in the pharmaceutical composition is stabilized by a non-protein excipient such as a polyvinylpyrrolidone, a disaccharides, a trisaccharide, a polysaccharide, an alcohol, a metal, an amino acid, a surfactant and/or a polyethylene glycol.

12 Claims, No Drawings

NON-PROTEIN STABILIZED CLOSTRIDIAL TOXIN PHARMACEUTICAL COMPOSITIONS

CROSS REFERENCE

This application is a nonprovisional utility application which claims priority to related provisional application No. 60/725,126, filed Oct. 6, 2005, the entire content of which application is incorporated herein by reference.

BACKGROUND

The present invention relates to Clostridial toxin pharmaceutical compositions. In particular, the present invention relates to Clostridial toxin pharmaceutical compositions with a non-protein excipient which functions to stabilize the Clostridial toxin (such as a botulinum toxin) present in the pharmaceutical composition.

A pharmaceutical composition is a formulation which contains at least one active ingredient (such as a Clostridial toxin) as well as, for example, one or more excipients, buffers, carriers, stabilizers, preservatives and/or bulking agents, and is suitable for administration to a patient to achieve a desired diagnostic result or therapeutic effect. The pharmaceutical compositions disclosed herein have diagnostic, therapeutic and/or research utility.

For storage stability and convenience of handling, a pharmaceutical composition can be formulated as a lyophilized (i.e. freeze dried) or vacuum dried powder which can be reconstituted with a suitable fluid, such as saline or water, prior to administration to a patient. Alternately, the pharmaceutical composition can be formulated as an aqueous solution or suspension. A pharmaceutical composition can contain a proteinaceous active ingredient. Unfortunately, a protein active ingredient can be very difficult to stabilize (i.e. maintained in a state where loss of biological activity is minimized), resulting therefore in a loss of protein and/or loss of protein activity during the formulation, reconstitution (if required) and during the period of storage prior to use of a protein containing pharmaceutical composition. Stability problems can occur because of protein denaturation, degradation, dimerization, and/or polymerization. Various excipients, such as albumin and gelatin have been used with differing degrees of success to try and stabilize a protein active ingredient present in a pharmaceutical composition. Additionally, cryoprotectants such as alcohols have been used to reduce protein denaturation under the freezing conditions of lyophilization.

Protein Excipients

Various proteins such as albumin and gelatin have been used to stabilize a botulinum toxin present in a pharmaceutical composition. Albumins are small, abundant plasma proteins. Human serum albumin has a molecular weight of about 69 kiloDaltons (kD) and has been used as a non-active ingredient in a pharmaceutical composition where it can serve as a bulk carrier and stabilizer of certain protein active ingredients present in a pharmaceutical composition.

The stabilization function of albumin in a pharmaceutical composition can be present both during the multi-step formulation of the pharmaceutical composition and upon the later reconstitution of the formulated pharmaceutical composition. Thus, stability can be imparted by albumin to a proteinaceous active ingredient in a pharmaceutical composition by, for example, (1) reducing adhesion (commonly referred to as "stickiness") of the protein active ingredient to surfaces, such as the surfaces of laboratory glassware, vessels, to the vial in which the pharmaceutical composition is reconstituted and to the inside surface of a syringe used to inject the pharmaceutical composition. Adhesion of a protein active ingredient to surfaces can lead to loss of active ingredient and to denaturation of the remaining retained protein active ingredient, both of which reduce the total activity of the active ingredient present in the pharmaceutical composition, and; (2) reducing denaturation of the active ingredient which can occur upon preparation of a low dilution solution of the active ingredient.

As well as being able to stabilize a protein active ingredient in a pharmaceutical composition, human serum albumin also has the advantage of generally negligible immunogenicity when injected into a human patient. A compound with an appreciable immunogenicity can cause the production of antibodies against it which can lead to an anaphylactic reaction and/or to the development of drug resistance, with the disease or disorder to be treated thereby becoming potentially refractory to the pharmaceutical composition which has an immunogenic component.

Recombinant albumin has been proposed as a stabilizer in a botulinum toxin pharmaceutical composition. Thus, published U.S. patent application number 2003 0118598 (Hunt) discloses uses of various excipients such as a recombinant albumin, collagen or a starch to stabilize a botulinum toxin present in a pharmaceutical composition.

Collagen is the most abundant protein in mammals comprising about one quarter of all protein in the body and it is the major constituent of connective tissues, such as skin, ligaments and tendons. Native collagen is a triple helix of three high molecular weight proteins. Each of the three protein chains comprising the collagen helix has more than 1400 amino acids. At least twenty five distinct types of collagens have been identified in humans.

Collagen has been used cosmetically as a filler material to treat of skin contour problems, such as to smooth smile line grooves and frown lines, folds between the eyebrows, wrinkles in the corners of the eyes and fine vertical creases above and below the lips. Collagen is also useful in smoothing certain post-surgical traumatic or acne scarring and viral pock marks, such as chicken pox marks. For such purposes the collagen is injected into the dermis to raise the skin.

Gelatin can be obtained by the hydrolysis of collagen. Gelatin has been used in some protein active ingredient pharmaceutical compositions as an albumin substitute. Notably, gelatin is a animal derived protein and therefore carries the same risk of potential infectivity which may be possessed by human serum albumin. Chinese patent CN 1215084 discusses an albumin free botulinum toxin type A formulated with native gelatin (a collagen hydrolysate), an animal derived protein, dextran and sucrose. U.S. Pat. No. 6,087,327 also discloses a composition of botulinum toxin types A and B formulated with native gelatin.

Unfortunately, despite their known stabilizing effects, significant drawbacks exist to the use of protein excipients, such as albumin or gelatin, in a pharmaceutical composition. For example albumin and gelatin are expensive and increasingly difficult to obtain. Furthermore, blood products or animal derived products such as albumin and gelatin, when administered to a patient can subject the patient to a potential risk of receiving blood borne pathogens or infectious agents. Thus, it is known that the possibility exists that the presence of an animal derived protein excipient in a pharmaceutical composition can result in inadvertent incorporation of infectious elements into the pharmaceutical composition. For example, it has been reported that use of human serum albumin may transmit prions into a pharmaceutical composition. A prion is a proteinaceous infectious particle which is hypothesized to arise as an abnormal conformational isoform from the same nucleic acid sequence which makes the normal protein. It has been further hypothesized that infectivity resides in a "recruitment reaction" of the normal isoform protein to the prion protein isoform at a post translational level. Apparently the normal endogenous cellular protein is induced to misfold into a pathogenic prion conformation.

Thus, it is desirable to find a suitable excipient which can be used to stabilize the botulinum toxin present, in a botulinum toxin pharmaceutical composition. Preferably, the botulinum toxin stabilizer is not a protein derived from an animal (i.e. mammalian) source.

Botulinum Toxin

The genus *Clostridium* has more than one hundred and twenty seven species, grouped by morphology and function. The anaerobic, gram positive bacterium *Clostridium botulinum* produces a potent polypeptide neurotoxin, botulinum toxin, which causes a neuroparalytic illness in humans and animals referred to as botulism. *Clostridium botulinum* and its spores are commonly found in soil and the bacterium can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of botulinum toxin (purified neurotoxin complex) type A is a $LD_{50}$ in mice. Interestingly, on a molar basis, botulinum toxin type A is 1.8 billion times more lethal than diphtheria, 600 million times more lethal than sodium cyanide, 30 million times more lethal than cobrotoxin and 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated $LD_{50}$ of botulinum toxin type A of 0.3 ng equals 1 U is corrected for the fact that about 0.05 ng of BOTOX® equals 1 unit). One unit (U) of botulinum toxin is defined as the $LD_{50}$ upon intraperitoneal injection into female Swiss Webster mice weighing 18-20 grams each. In other words, one unit of botulinum toxin is the amount of botulinum toxin that kills 50% of a group of female Swiss Webster mice. Seven generally immunologically distinct botulinum neurotoxins have been characterized, these being respectively botulinum neurotoxin serotypes A, B, $C_1$, D, E, F, and G, each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate $LD_{50}$ for botulinum toxin type A. The botulinum toxins apparently bind with high affinity to cholinergic motor neurons, are translocated into the neuron and block the presynaptic release of acetylcholine.

Botulinum toxins have been used in clinical settings for the treatment of neuromuscular disorders characterized by hyperactive skeletal muscles. Botulinum toxin type A was approved by the U.S. Food and Drug Administration in 1989 for the treatment of essential blepharospasm, strabismus and hemifacial spasm in patients over the age of twelve. Clinical effects of peripheral injection (i.e. intramuscular or subcutaneous) botulinum toxin type A are usually seen within one week of injection, and often within a few hours after injection. The typical duration of symptomatic relief (i.e. flaccid muscle paralysis) from a single intramuscular injection of botulinum toxin type A can be about three months to about six months.

Although all the botulinum toxins serotypes apparently inhibit release of the neurotransmitter acetylcholine at the neuromuscular junction, they do so by affecting different neurosecretory proteins and/or cleaving these proteins at different sites. Botulinum toxin A is a zinc endopeptidase which can specifically hydrolyze a peptide linkage of the intracellular, vesicle associated protein SNAP-25. Botulinum type E also cleaves the 25 kiloDalton (kD) synaptosomal associated protein (SNAP-25), but targets different amino acid sequences within this protein, as compared to botulinum toxin type A. Botulinum toxin types B, D, F and G act on vesicle-associated protein (VAMP, also called synaptobrevin), with each serotype cleaving the protein at a different site. Finally, botulinum toxin type $C_1$ has been shown to cleave both syntaxin and SNAP-25. These differences in mechanism of action may affect the relative potency and/or duration of action of the various botulinum toxin serotypes.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (H chain) and a cell surface receptor; the receptor is thought to be different for each serotype of botulinum toxin and for tetanus toxin. The carboxyl end segment of the H chain, $H_C$, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino end segment of the H chain, $H_N$, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin B, D, F, and G cause degradation of synaptobrevin (also called vesicle-associated membrane protein (VAMP)), a synaptosomal membrane protein. Most of the VAMP present at the cytosolic surface of the synaptic vesicle is removed as a result of any one of these cleavage events. Each toxin specifically cleaves a different bond.

The molecular weight of the botulinum toxin protein molecule, for all seven of the known botulinum toxin serotypes, is about 150 kD. Botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and $C_1$ are apparently produced as only a 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin protein and a non-toxin and non-toxic nonhemagglutinin protein. These two non-toxin proteins (which along with the botulinum toxin molecule can comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The toxin complexes can be dissociated into toxin protein and hemagglutinin proteins by treating the complex with red blood cells at pH 7.3. The toxin protein has a marked instability upon removal of the hemagglutinin protein.

All the botulinum toxin serotypes are made by *Clostridium botulinum* bacteria as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes $C_1$, D, and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine, CGRP and glutamate.

High quality crystalline botulinum toxin type A can be produced from the Hall A strain of *Clostridium botulinum* with characteristics of $\geq 3\times 10^7$ U/mg, an $A_{260}/A_{278}$ of less than 0.60 and a distinct pattern of banding on gel electrophoresis. The known Schantz process can be used to obtain crystalline botulinum toxin type A, as set forth in Schantz, E. J., et al, *Properties and use of Botulinum toxin and Other Microbial Neurotoxins in Medicine*, Microbiol Rev. 56: 80-99 (1992). Generally, the botulinum toxin type A complex can be isolated and purified from an anaerobic fermentation by cultivating *Clostridium botulinum* type A in a suitable medium. Raw toxin can be harvested by precipitation with sulfuric acid and concentrated by ultramicrofiltration. Purification can be carried out by dissolving the acid precipitate in calcium chloride. The toxin can then be precipitated with cold ethanol. The precipitate can be dissolved in sodium phosphate buffer and centrifuged. Upon drying there can then be obtained approximately 900 kD crystalline botulinum toxin type A complex with a specific potency of $3\times 10^7$ $LD_{50}$ U/mg or greater. This known process can also be used, upon separation out of the non-toxin proteins, to obtain pure botulinum toxins, such as for example: purified botulinum toxin type A with an approximately 150 kD molecular weight with a specific potency of $1-2\times 10^8$ $LD_{50}$ U/mg or greater; purified botulinum toxin type B with an approximately 156 kD molecular weight with a specific potency of $1-2\times 10^8$ $LD_{50}$ U/mg or greater, and; purified botulinum toxin type F with an approximately 155 kD molecular weight with a specific potency of $1-2\times 10^7$ $LD_{50}$ U/mg or greater.

Botulinum toxins and toxin complexes can be obtained from, for example, List Biological Laboratories, Inc., Campbell, Calif.; the Centre for Applied Microbiology and Research, Porton Down, U.K.; Wako (Osaka, Japan), as well as from Sigma Chemicals of St Louis, Mo. Commercially available botulinum toxin containing pharmaceutical compositions include BOTOX® (Botulinum toxin type A neurotoxin complex with human serum albumin and sodium chloride) available from Allergan, Inc., of Irvine, Calif. in 100 unit vials as a lyophilized powder to be reconstituted with 0.9% sodium chloride before use), DYSPORT® (Clostridium botulinum type A toxin haemagglutinin complex with human serum albumin and lactose in the formulation), available from Ipsen Limited, Berkshire, U.K. as a powder to be reconstituted with 0.9% sodium chloride before use), and MYOBLOC® (an injectable solution comprising botulinum toxin type B, human serum albumin, sodium succinate, and sodium chloride at about pH 5.6, available from Solstice Neurosciences, Inc., South San Francisco, Calif.).

The success of botulinum toxin type A to treat a variety of clinical conditions has led to interest in other botulinum toxin serotypes. Additionally, pure botulinum toxin has been used to treat humans. See e.g. Kohl A., et al., *Comparison of the effect of botulinum toxin A (Botox®) with the highly-purified neurotoxin (NT 201) in the extensor digitorum brevis muscle test*, Mov Disord 2000; 15(Suppl 3):165. Hence, a pharmaceutical composition can be prepared using a pure botulinum toxin.

The type A botulinum toxin is known to be soluble in dilute aqueous solutions at pH 4-6.8. At pH above about 7 the stabilizing nontoxic proteins dissociate from the neurotoxin, resulting in a gradual loss of toxicity, particularly as the pH and temperature rise. Schantz E. J., et al *Preparation and characterization of botulinum toxin type A for human treatment* (in particular pages 44-45), being chapter 3 of Jankovic, J., et al, *Therapy with Botulinum Toxin*, Marcel Dekker, Inc (1994).

European patent EP1112082 ("Stable liquid formulations of botulinum toxin"), issued Jul. 31, 2002 claims a stable liquid pharmaceutical botulinum toxin formulation comprising a buffer (pH 5-6) and a botulinum toxin, wherein the toxin formulation is stable as a liquid for at least one year at temperatures between 0-10 C or at least 6 months at temperatures between 10 and 30 C. Such a botulinum toxin pharmaceutical formulation (an embodiment of which is sold commercially under the tradename MYOBLOC® or NEUROBLOC® by Solstice Neurosciences, Inc., of San Diego, Calif.) is prepared as a liquid solution (no lyophilization or vacuum drying is carried out) which does not require reconstitution before use.

U.S. Pat. No. 5,512,547 (Johnson et al) entitled "Pharmaceutical Composition of Botulinum Neurotoxin and Method of Preparation" issued Apr. 30, 1996 and claims a pure botulinum type A formulation comprising albumin and trehalose, storage stable at 37 degrees C.

U.S. Pat. No. 5,756,468 (Johnson et al) issued May 26, 1998 ("Pharmaceutical Compositions of Botulinum Toxin or Botulinum Neurotoxin and Method of Preparation"), and claims a lyophilized botulinum toxin formulation comprising a thioalkyl, albumin and trehalose which can be stored between 25 degrees C. and 42 degrees C.

U.S. Pat. No. 5,696,077 (Johnson et al) entitled "Pharmaceutical Composition Containing Botulinum B Complex" issued Dec. 9, 1997 and claims a freeze dried, sodium chloride-free botulinum type B complex formation comprising a type B complex and a protein excipient.

Goodnough. M. C., et al., *Stabilization of botulinum toxin type A during lyophilization*, Appl Environ Microbiol 1992; 58(10):3426-3428, and; Goodnough M. C., et al., *Recovery of type-A botulinal toxin following lyophilization*, Acs Symposium Series 1994; 567(–):193-203, discloses.

Chinese patent application CN 1215084A discusses an albumin free botulinum toxin type A formulated with gelatin, an animal derived protein. U.S. Pat. No. 6,087,327 also discloses a composition of botulinum toxin types A and B formulated with gelatin. These formulations therefore do not eliminate the risk of transmitting an animal protein derived or accompanying infectious element.

It has been reported that BoNt/A has been used in various clinical settings, including as follows:

(1) about 75-125 units of BOTOX®[1] per intramuscular injection (multiple muscles) to treat cervical dystonia;

Available from Allergan, Inc., of Irving, Calif. under the tradename BOTOX®.

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Supp 4): S111-S1150: 1999), and in some circumstances for as long as 27 months. *The Laryngoscope* 109:1344-1346: 1999. However, the usual duration of an intramuscular injection of Botox® is typically about 3 to 4 months.

The success of botulinum toxin type A to treat a variety of clinical conditions has led to interest in other botulinum toxin serotypes. Additionally, pure botulinum toxin has been used in humans. See e.g. Kohl A., et al., *Comparison of the effect of botulinum toxin A (Botox®) with the highly-purified neurotoxin (NT 201) in the extensor digitorum brevis muscle test*, Mov Disord 2000; 15(Suppl 3):165. Hence, a pharmaceutical composition can be prepared using a pure botulinum toxin.

The botulinum toxin molecule (about 150 kDa), as well as the botulinum toxin complexes (about 300-900 kDa), such as the toxin type A complex are also extremely susceptible to denaturation due to surface denaturation, heat, and alkaline conditions. Inactivated toxin forms toxoid proteins which may be immunogenic. The resulting antibodies can render a patient refractory to toxin injection.

As with enzymes generally, the biological activities of the botulinum toxins (which are intracellular peptidases) are dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin must be stabilized with a stabilizing agent. To date, the only successful stabilizing agent for this purpose has been the animal derived proteins human serum albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, human serum albumin, and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. BOTOX® can be reconstituted with sterile, non-preserved saline prior to intramuscular injection. Each vial of BOTOX® contains about 100 units (U) of *Clostridium botulinum* toxin type A complex, 0.5 milligrams of human serum albumin and 0.9 milligrams of sodium chloride in a sterile, vacuum-dried form without a preservative.

To reconstitute vacuum-dried BOTOX® sterile normal saline without a preservative (0.9% Sodium Chloride injection) is used by drawing up the proper amount of diluent in the appropriate size syringe. Since BOTOX® is denatured by bubbling or similar violent agitation, the diluent is gently injected into the vial. For sterility reasons, BOTOX® should be administered within four hours after reconstitution. During this time period, reconstituted BOTOX® is stored in a refrigerator (2° to 8° C.). Reconstituted BOTOX® is clear, colorless and free of particulate matter. The vacuum-dried product is stored in a freezer at or below −5° C.

It has been reported that a suitable alternative to human serum albumin as a botulinum toxin stabilizer may be another protein or alternatively a low molecular weight (non-protein) compound. Carpender et al., *Interactions of Stabilizing Additives with Proteins During Freeze-Thawing and Freeze-Drying*, International Symposium on Biological Product Freeze-Drying and Formulation, 24-26 Oct. 1990; Karger (1992), 225-239.

Many substances commonly used as carriers and bulking agents in pharmaceutical compositions have proven to be unsuitable as non-protein excipients to stabilize the botulinum toxin present in a pharmaceutical composition. For example, the disaccharide cellobiose has been found to be unsuitable as a botulinum toxin stabilizer. Thus, it is known that the use of cellobiose as an excipient in conjunction with albumin and sodium chloride results in a much lower level of toxicity (10% recovery) after lyophilization of crystalline botulinum toxin type A with these excipients, as compared to the toxicity after lyophilization with only human serum albumin (>75% to >90% recovery). Goodnough et al., *Stabilization of Botulinum Toxin Type A During Lyophilization*, App & Envir. Micro. 58 (10) 3426-3428 (1992).

Furthermore, saccharides, including polysaccharides, are in general poor candidates to serve as protein stabilizers. Thus, it is known that a pharmaceutical composition containing a protein active ingredient is inherently unstable if the protein formulation comprises a saccharide (such as glucose or a polymer of glucose) or carbohydrates because proteins and glucose are known to interact together and to undergo the well-described Maillard reaction, due to the reducing nature of glucose and glucose polymers. Much work has been dedicated to mostly unsuccessful attempts at preventing this protein-saccharide reaction by, for example, reduction of moisture or use of non-reducing sugars. Significantly, the degradative pathway of the Maillard reaction can result in a therapeutic insufficiency of the protein active ingredient. A pharmaceutical formulation comprising protein and a reducing saccharide, carbohydrate or sugar, such as a glucose polymer, is therefore inherently unstable and cannot be stored for a long period of time without significant loss of the active ingredient protein's desired biological activity.

Particular high molecular weight polysaccharides (starches), such as hetastarch, have been proposed as stabilizers of the botulinum toxin present in a botulinum toxin pharmaceutical composition. See e.g. European patent EP 1 253 932, issued Apr. 27, 2005.

Notably, one of the reasons albumin or gelatin can function effectively as a stabilizer of a protein active ingredient in a pharmaceutical composition is because being proteins these stabilizers do not undergo the Maillard reaction with the protein active ingredient in a pharmaceutical composition. Hence, one would expect to find and to look for a substitute for these protein excipients used to stabilize the botulinum toxin present in a botulinum toxin pharmaceutical composition amongst other proteins.

Unique characteristics of botulinum toxin and its formulation into a suitable pharmaceutical composition constrain and hinder and render the search for a replacement for a protein stabilizer in a botulinum toxin containing pharmaceutical formulations problematic. Examples of four of these unique characteristics follow.

First, botulinum toxin is a relatively large protein for incorporation into a pharmaceutical formulation (the molecular weight of the botulinum toxin type A complex is 900 kD) and is therefore is inherently fragile and labile. The size of the toxin complex makes it much more friable and labile than smaller, less complex proteins, thereby compounding the formulation and handling difficulties if toxin stability is to be maintained. Hence, a botulinum toxin stabilizer must be able to interact with the toxin in a manner which does not denature, fragment or otherwise detoxify the toxin molecule or cause disassociation of the non-toxin proteins present in the toxin complex.

Second, as the most lethal known biological product, exceptional safety, precision, and accuracy is called for at all steps of the formulation of a botulinum toxin containing pharmaceutical composition. Thus, a botulinum toxin stabilizer should not itself be toxic or difficult to handle so as to not exacerbate the already extremely stringent botulinum toxin containing pharmaceutical composition formulation requirements.

Third, since botulinum toxin was the first microbial toxin to be approved (by the FDA in 1989) for injection for the treatment of human disease, specific protocols had to be developed and approved for the culturing, bulk production, formulation into a pharmaceutical and use of botulinum toxin. Important considerations are toxin purity and dose for injection. The production by culturing and the purification must be carried out so that the toxin is not exposed to any substance that might contaminate the final product in even trace amounts and cause undue reactions in the patient. These restrictions require culturing in simplified medium without the use of animal meat products and purification by procedures not involving synthetic solvents or resins. Preparation of toxin using enzymes, various exchangers, such as those present in chromatography columns and synthetic solvents can introduce contaminants and are therefore excluded from preferred formulation steps. Furthermore, botulinum toxin type A is readily denatured at temperatures above 40 degrees C., loses toxicity when bubbles form at the air/liquid interface, and denatures in the presence of nitrogen or carbon dioxide.

Fourth, particular difficulties exist to stabilize botulinum toxin type A, because type A consists of a toxin molecule of about 150 kD in noncovalent association with nontoxin proteins weighing about 750 kD. The nontoxin proteins are believed to preserve or help stabilize the secondary and tertiary structures upon which toxicity is dependant. Procedures or protocols applicable to the stabilization of nonproteins or to relatively smaller proteins are not applicable to the problems inherent with stabilization of the botulinum toxin complexes, such as the 900 kD botulinum toxin type A complex. Thus while from pH 3.5 to 6.8 the type A toxin and non toxin proteins are bound together noncovalently, under slightly alkaline conditions (pH>7.1) the very labile toxin is released from the toxin complex. As set forth previously, pure botulinum toxin (i.e. the 150 kD molecule) has been proposed as the active ingredient in a pharmaceutical composition.

In light of the unique nature of botulinum toxin and the requirements set forth above, the probability of finding a suitable non-protein stabilizer for the protein stabilizers used in botulinum toxin containing pharmaceutical compositions must realistically be seen to approach zero. Prior to the present invention, only the animal derived proteins, human serum albumin and gelatin, had been known to have utility as suitable stabilizers of the botulinum toxin present in a pharmaceutical formulation. Thus, albumin, by itself or with one or more additional substances such as sodium phosphate or sodium citrate, is known to permit high recovery of toxicity of botulinum toxin type A after lyophilization. Unfortunately, as already set forth, human serum albumin, as a pooled blood product, can, at least potentially, carry infectious or disease causing elements when present in a pharmaceutical composition. Indeed, any animal product or protein such as human serum albumin or gelatin can also potentially contain pyrogens or other substances that can cause adverse reactions upon injection into a patient.

What is needed therefore is a Clostridial toxin pharmaceutical compositions wherein the Clostridial toxin (such as a botulinum toxin) is stabilized by a non-protein excipient.

SUMMARY

The present invention meets this need and provides a botulinum toxin pharmaceutical composition which is stabilized by a non-protein excipient.

DEFINITIONS

As used herein, the words or terms set forth below have the following definitions.

"About" means that the item, parameter or term so qualified encompasses a range of plus or minus ten percent above and below the value of the stated item, parameter or term.

"Administration", or "to administer" means the step of giving (i.e. administering) a pharmaceutical composition to a subject. The pharmaceutical compositions disclosed herein are "locally administered" by e.g. intramuscular (i.m.), intradermal, subcutaneous administration, intrathecal administration, intraperitoneal (i.p.) administration, topical (transdermal) and implantation (i.e. of a slow-release device such as polymeric implant or miniosmotic pump) routes of administration.

"Animal protein free" means the absence of blood derived, blood pooled and other animal derived products or compounds. "Animal" means a mammal (such as a human), bird, reptile, fish, insect, spider or other animal species. "Animal" excludes microorganisms, such as bacteria. Thus, an animal protein free pharmaceutical composition within the scope of my invention can include a Clostridial neurotoxin. For example, an animal protein free pharmaceutical composition means a pharmaceutical composition which is either substantially free or essentially free or entirely free of a serum derived albumin, gelatin and other animal derived proteins, such as immunoglobulins. An example of an animal protein free pharmaceutical composition is a pharmaceutical composition which comprises or which consists of a botulinum toxin (as the active ingredient) and a suitable polysaccharide as a stabilizer or excipient.

"Botulinum toxin" means a neurotoxin produced by *Clostridium botulinum*, as well as a botulinum toxin (or the light chain or the heavy chain thereof) made recombinantly by a non-Clostridial species. The phrase "botulinum toxin", as used herein, encompasses the botulinum toxin serotypes A, B, C, D, E, F and G. Botulinum toxin, as used herein, also encompasses both a botulinum toxin complex (i.e. the 300, 600 and 900 kDa complexes) as well as the purified botulinum toxin (i.e. about 150 kDa). "Purified botulinum toxin" is defined as a botulinum toxin that is isolated, or substantially isolated, from other proteins, including proteins that form a botulinum toxin complex. A purified botulinum toxin may be greater than 95% pure, and preferably is greater than 99% pure. The botulinum $C_2$ and $C_3$ cytotoxins, not being neurotoxins, are excluded from the scope of the present invention.

"Clostridial neurotoxin" means a neurotoxin produced from, or native to, a Clostridial bacterium, such as *Clostridium botulinum, Clostridium butyricum* or *Clostridium beratti*, as well as a Clostridial neurotoxin made recombinantly by a non-Clostridial species.

"Entirely free (i.e. "consisting of" terminology) means that within the detection range of the instrument or process being used, the substance cannot be detected or its presence cannot be confirmed.

"Essentially free" (or "consisting essentially of") means that only trace amounts of the substance can be detected.

"Modified botulinum toxin" means a botulinum toxin that has had at least one of its amino acids deleted, modified, or replaced, as compared to a native botulinum toxin. Additionally, the modified botulinum toxin can be a recombinantly produced neurotoxin, or a derivative or fragment of a recombinantly made neurotoxin. A modified botulinum toxin retains at least one biological activity of the native botulinum toxin, such as, the ability to bind to a botulinum toxin receptor, or the ability to inhibit neurotransmitter release from a neuron. One example of a modified botulinum toxin is a botulinum toxin that has a light chain from one botulinum toxin serotype (such as serotype A), and a heavy chain from a different botulinum toxin serotype (such as serotype B). Another example of a modified botulinum toxin is a botulinum toxin coupled to a neurotransmitter, such as substance P.

"Pharmaceutical composition" means a formulation in which an active ingredient can be a Clostridial neurotoxin, such as a botulinum toxin. The word "formulation" means that there is at least one additional ingredient in the pharmaceutical composition besides a Clostridial neurotoxin active ingredient. A pharmaceutical composition is therefore a formulation which is suitable for diagnostic or therapeutic administration (i.e. by intramuscular or subcutaneous injection or by insertion of a depot or implant) to a subject, such as a human patient. The pharmaceutical composition can be: in a lyophilized or vacuum dried condition; a solution formed after reconstitution of the lyophilized or vacuum dried pharmaceutical composition with saline or water, or; as a solution which does not require reconstitution. The neurotoxin active ingredient can be one of the botulinum toxin serotypes A, B, $C_1$, D, E, F or G or a tetanus toxin, all of which can be made natively by Clostridial bacteria. As stated, a pharmaceutical composition can be liquid or solid, for example vacuum-dried. The constituent ingredients of a pharmaceutical composition can be included in a single composition (that is all the constituent ingredients, except for any required reconstitution fluid, are present at the time of initial compounding of the pharmaceutical composition) or as a two-component system, for example a vacuum-dried composition reconstituted with a diluent such as saline which diluent contains an ingredient not present in the initial compounding of the pharmaceutical composition. A two-component system provides the benefit of allowing incorporation of ingredients which are not sufficiently compatible for long-term shelf storage with the first component of the two component system. For example, the reconstitution vehicle or diluent may include a preservative which provides sufficient protection against microbial growth for the use period, for example one-week of refrigerated storage, but is not present during the two-year freezer storage period during which time it might degrade the toxin. Other ingredients, which may not be compatible with a Clostridial toxin or other ingredients for long periods of time, may be incorporated in this manner; that is, added in a second vehicle (i.e. in the reconstitution fluid) at the approximate time of use.

"Stabilizer" (or "primary stabilizer") is a chemical agent that assists to preserve or maintain the biological structure (i.e. the three dimensional conformation) and/or biological activity of a protein (such as a Clostridial neurotoxin, such as a botulinum toxin). The stabilizers used herein are non-proteins. The primary stabilizer can be a synthetic agent that would not produce an immunogenic response (or produces an attenuated immune response) in a subject receiving a composition containing the primary stabilizer. Additional stabilizers may also be included in a pharmaceutical composition. These additional or secondary stabilizers may be used alone or in combination with the primary stabilizers. Exemplary secondary stabilizers include, but are not limited to non-oxidizing amino acid derivatives (such as a tryptophan derivate, such as N-acetyl-tryptophan ("NAT")), caprylate (i.e. sodium caprylate), a polysorbate (i.e. P80), amino acids, and divalent metal cations such as zinc. A pharmaceutical composition can also include preservative agents such as benzyl alcohol, benzoic acid, phenol, parabens and sorbic acid.

"Stabilizing", "stabilizes", or "stabilization" mean that a pharmaceutical active ingredient ("PAI") retains at least 20% and up to 100% of its biological activity (which can be assessed as potency or as toxicity by an in vivo $LD_{50}$ or $ED_{50}$ measure) in the presence of a compound which is stabilizing, stabilizes or which provides stabilization to the PAI. For example, upon (1) preparation of serial dilutions from a bulk or stock solution, or (2) upon reconstitution with saline or water of a lyophilized, or vacuum dried botulinum toxin containing pharmaceutical composition which has been stored at or below about −2 degrees C. for between six months and four years, or (3) for an aqueous solution botulinum toxin containing pharmaceutical composition which has been stored at between about 2 degrees and about 8 degrees C. for from six months to four years, the botulinum toxin present in the reconstituted or aqueous solution pharmaceutical composition has (in the presence of a compound which is stabilizing, stabilizes or which provides stabilization to the PAI) greater than about 20% and up to about 100% of the potency or toxicity that the biologically active botulinum toxin had prior to being incorporated into the pharmaceutical composition.

"Substantially free" means present at a level of less than one percent by weight of the pharmaceutical composition.

"Therapeutic formulation" means a formulation can be used to treat and thereby alleviate a disorder or a disease, such as a disorder or a disease characterized by hyperactivity (i.e. spasticity) of a peripheral muscle.

The botulinum toxin can be present as a botulinum toxin complex (i.e. as an approximately 300 to about 900 kiloDalton complex depending upon the particular botulinum toxin serotype) or the botulinum toxin can be is present as a pure or purified botulinum toxin (i.e. as the botulinum toxin molecule of about 150 kiloDaltons).

The pharmaceutical compositions disclosed herein can have a pH of between about 5 and 7.3 when reconstituted or upon injection.

My invention can be practiced utilizing a composition that comprises a botulinum toxin type A. In other embodiments of the invention, the foregoing methods may be practiced with a composition that comprises botulinum toxin type B. In further embodiments of the invention, the methods may be practiced with a composition that comprises a plurality of botulinum toxin serotypes, such as botulinum toxin serotypes selected from the group consisting of botulinum toxin serotypes A, B, $C_1$, D, E, F and G. In certain embodiments of the invention, purified botulinum toxins, may be used. In other embodiments, modified botulinum toxins may be used.

In yet additional embodiments of the invention, the compositions used in the foregoing methods can be administered intramuscularly to the patient. In other embodiments, the compositions can be administered subcutaneously and/or intrathecally.

My invention encompasses a pharmaceutical composition comprising (or consisting of or consisting essentially of) a botulinum toxin and a polyvinylpyrrolidone. The botulinum toxin is a biologically active botulinum toxin and the botulinum toxin is selected from the group consisting of the botulinum toxins types A, B, C, D, E, F and G. Preferably, the botulinum toxin is a botulinum toxin type A. A function of the polyvinylpyrrolidone present in the pharmaceutical composition is to stabilize the botulinum toxin.

My invention also encompasses a pharmaceutical composition comprising (or consisting of or consisting essentially of) a botulinum toxin, and between about 5 grams and about 20 grams of a polyvinylpyrrolidone for each about 100 units of the botulinum toxin.

My invention also encompasses a pharmaceutical composition comprising (or consisting of or consisting essentially of) a botulinum toxin, wherein the botulinum toxin is not stabilized by a protein excipient, and a polyvinylpyrrolidone, wherein the potency of the botulinum toxin is at least about 40% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, and a polyvinylpyrrolidone, wherein the potency of the botulinum toxin is at least about 50% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a to polyvinylpyrrolidone, and a disaccharide, wherein the potency of the botulinum toxin is at least about 40% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyvinylpyrrolidone, and a disaccharide, wherein the potency of the botulinum toxin is at least about 50% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyvinylpyrrolidone, and a disaccharide, wherein the potency of the botulinum toxin is at least about 60% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyvinylpyrrolidone, and a disaccharide, wherein the potency of the botulinum toxin is at least about 70% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyvinylpyrrolidone, and a polyethylene glycol, wherein the potency of the botulinum toxin is at least about 40% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a compound selected from the group consisting of a first monosaccharide, a first disaccharide, a first trisaccharide, and a first alcohol made by reducing the first monosaccharide, and a compound selected from the group of compounds consisting of a polyethylene glycol, a second monosaccharide, a second disaccharide, a second trisaccharide, a metal, a second alcohol, and an amino acid, wherein the second monosaccharide, the second disaccharide and the second trisaccharide are different from respectively the first monosaccharide, the first disaccharide, and the first trisaccharide, wherein the potency of the botulinum toxin at least about 40% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 20% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 30% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 40% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 50% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 60% of the theoretical maximum potency of the botulinum toxin.

My invention also encompasses a pharmaceutical composition comprising (or consisting of or consisting essentially of) a botulinum toxin, wherein the botulinum toxin is not stabilized by a protein excipient, a polyethylene glycol, and a compound selected from the group of compounds consisting of a monosaccharide, a disaccharide, a trisaccharide, a metal, an alcohol, and an amino acid, wherein the potency of the botulinum toxin is at least about 70% of the theoretical maximum potency of the botulinum toxin.

DESCRIPTION

The present invention is based upon the discovery that a Clostridial toxin pharmaceutical composition, with a stabilized Clostridial toxin, can be made using a non-protein excipient as the primary stabilizer of the Clostridial toxin.

I have discovered that a suitable replacement for a protein excipient, such as albumin or gelatin in a Clostridial toxin pharmaceutical composition can be a non-protein compound.

The non-protein excipient used in the present invention can impart stability to a neurotoxin active ingredient, such as a botulinum toxin, present in the pharmaceutical composition by: (1) reducing adhesion (commonly referred to as "stickiness") of the botulinum toxin to surfaces, such as the surfaces of laboratory glassware, vessels, the vial in which the pharmaceutical composition is reconstituted and the inside surface of the syringe used to inject the pharmaceutical composition. Adhesion of the botulinum toxin to surfaces can lead to loss of botulinum toxin and to denaturation of retained botulinum toxin, both of which reduce the toxicity of the botulinum toxin present in the pharmaceutical composition. (2) reducing the denaturation of the botulinum toxin and/or dissociation of the botulinum toxin from other non-toxin proteins present in the botulinum toxin complex, which denaturation and/or dissociation activities can occur because of the low dilution of the botulinum toxin present in the pharmaceutical composition (i.e. prior to lyophilization or vacuum drying) and in the reconstituted pharmaceutical composition. (3) reducing loss of botulinum toxin (i.e. due to denaturation or dissociation from non-toxin proteins in the complex) during the considerable pH and concentration changes which take place during preparation, processing and reconstitution of the pharmaceutical composition.

The three types of botulinum toxin stabilizations provided by the non-protein stabilizers disclosed herein conserve and preserve the botulinum toxin with it native toxicity prior to injection of the pharmaceutical composition.

In certain embodiments of the invention, the pharmaceutical compositions of the invention may comprise a plurality of botulinum toxin serotypes. In other words, the composition may include two or more different botulinum toxin serotypes. For example, a composition may include botulinum toxin serotypes A and B. In another embodiment, a composition may include botulinum toxin serotypes A and E. Using a combination of botulinum toxin serotypes will permit caregivers to customize the composition to achieve a desired effect based on the condition being treated. In an additional embodiment of the invention, the composition may comprise a modified botulinum toxin. The modified botulinum toxin will preferably inhibit the release of neurotransmitter from a neuron, but may have a greater or lower potency than the native botulinum toxin, or may have a greater or lower biological effect than the native botulinum toxin. Because the compositions of the invention may be used for relatively long-term treatment of animals, the compositions may be provided in a relatively pure form. In one embodiment, the compositions are of a pharmaceutical grade. In certain embodiments, the clostridial neurotoxin has a greater than 95% purity. In additional embodiments, the clostridial neurotoxin has a purity greater than 99%.

My invention also encompasses addition of a preservative, either in the diluent or formulation itself, to allow extended storage. A preferred preservative is preserved saline containing benzyl alcohol.

The pharmaceutical compositions of the invention can be administered using conventional modes of administration. In preferred embodiments of the invention, the compositions are administered intramuscularly or subcutaneously to the subject. In other embodiments, the compositions of the invention may be administered intrathecally. In addition, the compositions of the invention may be administered with one or more analgesic or anesthetic agents.

The most effective mode of administration and dosage regimen for the compositions of this invention depends upon the type, severity, and course of the condition being treated, the animal's health and response to treatment, and the judgment of the treating doctor. Accordingly, the methods and dosages of the compositions should be tailored to the individual subject.

By way of example, and not by way of limitation, it may be preferred to administer the composition of the invention intramuscularly to reduce a muscle spasm.

My invention also encompasses a pharmaceutical composition comprising a botulinum toxin and a collagen for use to treat a variety of conditions wherein the botulinum toxin acts to paralyze a muscle and the collagen acts to provide a dermal filler.

Compositions containing other serotypes of botulinum toxin may contain different dosages of the botulinum toxin. For example, botulinum toxin type B may be provided in a composition at a greater dose than a composition containing botulinum toxin type A. In one embodiment of the invention, botulinum toxin type B may be administered in an amount between about 1 U/kg and 150 U/kg. Botulinum toxin type B may also be administered in amounts of up to 20,000 U (mouse units, as described above). In another embodiment of the invention, botulinum toxin types E or F may be administered at concentrations between about 0.1 U/kg and 150 U/kg. In addition, in compositions containing more than one type of botulinum toxin, each type of botulinum toxin can be provided in a relatively smaller dose than the dose typically used for a single botulinum toxin serotype. The combination of botulinum toxin serotypes may then provide a suitable degree and duration of paralysis without an increase in diffusion of the neurotoxins (e.g. see U.S. Pat. No. 6,087,327).

EXAMPLES

The following examples set forth specific embodiments of the present invention and are not intended to limit the scope of the invention.

In the Examples below the well known mouse lethal dose$_{50}$ assay (the "MLD50 assay") was used to determine botulinum toxin potency. Depending on the circumstances, "potency" can mean the recovered potency of the botulinum toxin or the potency of the botulinum toxin prior to lyophilization. Recovered potency is synonymous with reconstitution potency, recovery potency and with potency upon reconstitution. The MLD50 assay provides a determination of the potency of a botulinum toxin in terms of its mouse 50% lethal dose or "LD50". Thus, one unit (U) of a botulinum toxin is defined as the amount of botulinum toxin which upon intraperitoneal injection kills 50% (i.e. a $LD_{50}$) of a group of female Swiss Weber mice weighing 17-22 grams each at the start of the assay. The MLD50 assay is a validated method for measuring the potency of a reconstituted botulinum toxin or of a reconstituted botulinum toxin formulation. Each mouse is held in a supine position with its head tilted down and is injected intraperitoneally into the lower right abdomen at an angle of about 30 degrees using a 25 to 27 gauge ⅜" to ⅝" needle with one of several serial dilutions of the botulinum toxin in normal saline. The death rates over the ensuing 72 hours for each dilution are recorded. A minimum of six dilutions at 1.33 dose intervals are prepared and typically ten animals are used in each dosage group (60 mice employed therefore). Two reference standard assays are carried out concurrently (additional 60 mice employed). The dilutions are prepared so that the most concentrated dilution produces a death rate of at least 80% of the mice injected, and the least concentration dilution produces a death rate no greater than 20% of the mice injected. There must be a minimum of four dilutions that fall within the monotone decreasing range of the death rates. The monotone decreasing range commences with a death rate of no less than 80%. Within the four or more monotone decreasing rates, the two largest and the two smallest rates must be decreasing (i.e. not equivalent). The dilution at which 50% of the mice die within the three day post injection observation period is defined as a dilution which comprises one unit (1 U) of the botulinum toxin. A refined MLD50 assay has been developed which uses fewer (five instead of six) dilutions at 1.15 dose intervals and fewer mice (six instead of ten) per dilution tested.

Example 1

Botulinum Toxin Pharmaceutical Composition Containing Human Serum Albumin (Prior Art)

A botulinum toxin type A complex was obtained from a culture of the Hall strain of *Clostridium botulinum* grown in a medium containing N-Z amine and yeast extract. The botulinum toxin type A complex was purified from the culture solution by a series of acid precipitations to a crystalline complex consisting of the active high molecular weight toxin protein and an associated hemagglutinin protein. The crystalline complex was then re-dissolved in a solution containing saline and albumin and sterile filtered (0.2 microns) prior to vacuum-drying. The vacuum dried composition was reconstituted with sterile, non-preserved saline prior to injection. Each vial of vacuum dried composition contains about 100 units (U) of *Clostridium botulinum* toxin type A complex, 0.5 milligrams of human serum albumin and 0.9 milligrams of sodium chloride in a sterile, vacuum-dried form without a preservative. This pharmaceutical composition is sold commercially under the trade name BOTOX® in 100 unit vials for reconstitution with saline prior to injection.

Example 2

Non-Protein Stabilized Botulinum Toxin Formulations

Experiments were carried out to prepare multiple botulinum toxin formulations with one or more different non-protein stabilizing excipients. All of the formulations were compounded, lyophilized, reconstituted and potency assessed in the same manner, and with the same type of botulinum toxin used in each formulation, expect that each formulation was prepared with a different non-protein excipient or excipients or with a different amount of the non-protein excipient or of the non-protein excipients present in the botulinum toxin formulation.

The non-protein excipients used (separately or in combination) in the formulations made in these experiments included: a polyvinylpyrrolidone (also called povidone, such as Kollidon 17); various disaccharides (such as lactose and trehalose); a trisaccharide (such as raffinose); a polysaccharide (such as inulin); an alcohol (such as an alcohol made by reducing a monosaccharide [such as fructose] or such as mannitol); a metal (such as zinc); an amino acid (such as glycine), and; a polyethylene glycol (such as poloxamer 188 and/or PEG 3350). Since a protein is a polyamino acid, use of one or more single amino acids in the formulations set forth herein did not provide a protein excipient in these formulations.

The formulations disclosed in this Example were made by first adding the indicated amount of the non-protein excipient(s) to sterile water for injection to form a solution. Next between 100 to 200 units of a botulinum toxin type A complex (obtained by anaerobic fermentation of the Hall stain of *Clostridium botulinum* followed by purification of the botulinum toxin released into and removed from the fermentation medium. See e.g. Example 1 above and Schantz E. J. et al., *Properties and use of botulinum toxin and other microbial neurotoxins in medicine*, Microbiol Rev 1992 March; 56(1): 80-99) was added to the solution, to thereby form a botulinum toxin formulation, which can be synonymously be referred to as a botulinum toxin pharmaceutical composition, or simply as a formulation. The potency prior to lyophilization of the botulinum toxin used was determined by the mouse LD50 assay prior to the addition of the botulinum toxin to the solution, and was between about 100 units and about 200 units.

The formulations were then lyophilized (or freeze dried or vacuum dried) followed by reconstitution with normal saline. Recovered potency of the botulinum toxin present in the reconstituted formulation was determined by application of the same mouse LD50 assay.

"% Recovery" in Tables 1 to 5 is the potency of the botulinum toxin after reconstitution (therefore "recovered potency") expressed as a percent of the potency of the botulinum toxin before lyophilization of the formulation. Thus, for example, a % Recovery of 60% means that the potency of the botulinum toxin after reconstitution was 60% of the potency of the botulinum toxin prior to lyophilization. The maximum theoretical recovered potency is 100%. The % Recovery values were obtained by reconstitution right after the formulation was lyophilized.

Tables 1 to 6 present the results of the experiments carried out in this Example where the formulations were made as set forth above.

TABLE 1

Botulinum Toxin Formulations with a Single Non-Protein Excipient and No Recovered Potency

| Excipient | Amount (mg) | % Recovery |
|---|---|---|
| 1. Kollidon 17 | 0.5 | 0 |
| 2. Kollidon 17 | 50 | 0 |
| 3. Kollidon 17 | 100 | 0 |
| 4. Kollidon 17 | 250 | 0 |
| 5. Lactose | 5 | 0 |
| 6. Sucrose | 5 | 0 |
| 7. Sucrose | 10 | 0 |
| 8. Sucrose | 50 | 0 |
| 9. Sucrose | 100 | 0 |
| 10. Sucrose | 250 | 0 |
| 11. Glycine | 5 | 0 |
| 12. Glycine | 10 | 0 |
| 13. Glycine | 50 | 0 |
| 14. ZnCl | 0.1 | 0 |
| 15. ZnCl | 0.01 | 0 |
| 16. ZnCl | 0.001 | 0 |
| 17. Mannitol | 5 | 0 |
| 18. Mannitol | 10 | 0 |
| 19. Mannitol | 50 | 0 |
| 20. Inulin | 5 | 0 |
| 21. Inulin | 10 | 0 |
| 22. Inulin | 50 | 0 |
| 23. Trehalose | 5 | 0 |
| 24. Trehalose | 10 | 0 |
| 25. Trehalose | 50 | 0 |
| 26. Raffinose | 5 | 0 |
| 27. Raffinose | 10 | 0 |
| 28. Raffinose | 50 | 0 |
| 29. PEG 3350 | 50 | 0 |
| 30. Poloxamer 188 | 50 | 0 |

TABLE 2

Botulinum Toxin Formulations with a Single Non-Protein Excipient and a Recovered Potency

| Excipient | Amount (mg) | % Recovery |
|---|---|---|
| 1. Kollidon 17 | 5 | 48 |
| 2. Kollidon 17 | 10 | 52 |
| 3. Kollidon 17 | 20 | 39 |
| 4. Lactose | 10 | 15 |
| 5. Lactose | 50 | 35 |

TABLE 3

Botulinum Toxin Formulations with a Two Non-Protein Excipients and No Recovered Potency

| Excipient 1 | Excipient 2 | Amount 1 (mg) | Amount 2 (mg) | % Recovery |
|---|---|---|---|---|
| 1. Kollidon 17 | Lactose | 0.5 | 0.5 | 0 |
| 2. Kollidon 17 | Lactose | 50 | 0.5 | 0 |
| 3. Kollidon 17 | Lactose | 100 | 5 | 0 |
| 4. Kollidon 17 | Sucrose | 0.5 | 0.5 | 0 |
| 5. Kollidon 17 | Sucrose | 50 | 0.5 | 0 |
| 6. Kollidon 17 | Sucrose | 0.5 | 5 | 0 |
| 7. Kollidon 17 | Sucrose | 100 | 5 | 0 |
| 8. Sucrose | ZnCl | 50 | 0.000005 | 0 |
| 9. Mannitol | ZnCl | 50 | 0.000005 | 0 |
| 10. Mannitol | PEG 3350 | 5 | 50 | 0 |
| 11. Mannitol | Sucrose | 50 | 5 | 0 |
| 12. Mannitol | Sucrose | 5 | 50 | 0 |
| 13. Mannitol | ZnCl | 50 | 1 | 0 |
| 14. Mannitol | ZnCl | 50 | 0.1 | 0 |
| 15. Mannitol | ZnCl | 5 | 1 | 0 |
| 16. Mannitol | Trehalose | 50 | 50 | 0 |
| 17. Mannitol | Trehalose | 50 | 5 | 0 |
| 18. Mannitol | Trehalose | 5 | 50 | 0 |
| 19. Sucrose | Glycine | 50 | 50 | 0 |
| 20. Sucrose | Glycine | 50 | 5 | 0 |
| 21. Sucrose | Glycine | 5 | 50 | 0 |
| 22. Sucrose | ZnCl | 50 | 1 | 0 |
| 23. Sucrose | ZnCl | 50 | 0.1 | 0 |
| 24. Sucrose | ZnCl | 5 | 1 | 0 |
| 25. Sucrose | Trehalose | 50 | 50 | 0 |
| 26. Sucrose | Trehalose | 50 | 5 | 0 |
| 27. Sucrose | Trehalose | 5 | 50 | 0 |
| 28. ZnCl | Glycine | 1 | 50 | 0 |
| 29. ZnCl | Glycine | 1 | 5 | 0 |
| 30. ZnCl | Glycine | 0.1 | 50 | 0 |
| 31. Poloxamer 188 | ZnCl | 50 | 1 | 0 |
| 32. Poloxamer 188 | ZnCl | 5 | 1 | 0 |
| 33. Trehalose | ZnCl | 50 | 1 | 0 |

TABLE 3-continued

Botulinum Toxin Formulations with a Two Non-Protein Excipients and No Recovered Potency

| Excipient 1 | Excipient 2 | Amount 1 (mg) | Amount 2 (mg) | % Recovery |
|---|---|---|---|---|
| 34. Trehalose | ZnCl | 5 | 1 | 0 |
| 35. Trehalose | ZnCl | 50 | 0.1 | 0 |
| 36. PEG 3350 | ZnCl | 50 | 1 | 0 |
| 37. PEG 3350 | ZnCl | 50 | 0.1 | 0 |
| 38. Poloxamer 188 | Glycine | 5 | 50 | 0 |
| 39. Poloxamer 188 | PEG 3350 | 50 | 50 | 0 |
| 40. Poloxamer 188 | PEG 3350 | 50 | 5 | 0 |
| 41. Poloxamer 188 | PEG 3350 | 5 | 50 | 0 |
| 42. Trehalose | Glycine | 50 | 50 | 0 |
| 43. Trehalose | Glycine | 50 | 5 | 0 |
| 44. Trehalose | Glycine | 5 | 50 | 0 |
| 45. Trehalose | PEG 3350 | 50 | 50 | 0 |
| 46. PEG 3350 | Glycine | 50 | 50 | 0 |
| 47. PEG 3350 | Glycine | 50 | 5 | 0 |
| 48. PEG 3350 | Glycine | 5 | 50 | 0 |

TABLE 4

Botulinum Toxin Formulations with a Two Non-Protein Excipients and a Recovered Potency

| Excipient 1 | Excipient 2 | Amount 1 (mg) | Amount 2 (mg) | % Recovery |
|---|---|---|---|---|
| 1. Kollidon 17 | Lactose | 5 | 0.5 | 65 |
| 2. Kollidon 17 | Lactose | 10 | 0.5 | 47 |
| 3. Kollidon 17 | Lactose | 20 | 0.5 | 65 |
| 4. Kollidon 17 | Lactose | 0.5 | 5 | 52 |
| 5. Kollidon 17 | Lactose | 5 | 5 | 57 |
| 6. Kollidon 17 | Lactose | 10 | 5 | 65 |
| 7. Kollidon 17 | Lactose | 20 | 5 | 49 |
| 8. Kollidon 17 | Lactose | 50 | 5 | 52 |
| 9. Kollidon 17 | Sucrose | 5 | 0.5 | 58 |
| 10. Kollidon 17 | Sucrose | 10 | 0.5 | 46 |
| 11. Kollidon 17 | Sucrose | 20 | 0.5 | 49 |
| 12. Kollidon 17 | Sucrose | 5 | 5 | 49 |
| 13. Kollidon 17 | Sucrose | 10 | 5 | 58 |
| 14. Kollidon 17 | Sucrose | 20 | 5 | 47 |
| 15. Kollidon 17 | Sucrose | 50 | 5 | 39 |
| 16. Kollidon 17 | Sucrose | 250 | 250 | 39 |
| 17. Kollidon 17 | Sucrose | 10 | 250 | 58 |
| 18. Kollidon 17 | PEG 3350 | 50 | 50 | 35 |
| 19. Lactose | PEG 3350 | 50 | 50 | 53 |
| 20. Lactose | Sucrose | 50 | 50 | 27 |
| 21. Lactose | ZnCl | 50 | 0.000005 | 19 |
| 22. Lactose | Mannitol | 50 | 50 | 23 |
| 23. Sucrose | Mannitol | 50 | 50 | 24 |
| 24. Mannitol | PEG 3350 | 50 | 50 | 26 |
| 25. Mannitol | PEG 3350 | 50 | 5 | 30 |
| 26. Mannitol | Sucrose | 50 | 50 | 29 |
| 27. Mannitol | Poloxamer 188 | 50 | 50 | 33 |
| 28. Mannitol | Poloxamer 188 | 50 | 5 | 35 |
| 29. Mannitol | Poloxamer 188 | 5 | 50 | 30 |
| 30. Sucrose | Poloxamer 188 | 50 | 50 | 59 |
| 31. Sucrose | Poloxamer 188 | 50 | 5 | 43 |
| 32. Sucrose | Poloxamer 188 | 5 | 50 | 55 |
| 33. Sucrose | PEG 3350 | 50 | 50 | 44 |
| 34. Sucrose | PEG 3350 | 50 | 5 | 41 |
| 35. Sucrose | PEG 3350 | 5 | 50 | 35 |
| 36. Poloxamer 188 | ZnCl | 50 | 0.1 | 38 |
| 37. PEG 3350 | ZnCl | 5 | 1 | 23 |
| 38. Poloxamer 188 | Glycine | 50 | 50 | 26 |
| 39. Poloxamer 188 | Glycine | 50 | 5 | 33 |
| 40. Poloxamer 188 | Trehalose | 50 | 50 | 53 |
| 41. Poloxamer 188 | Trehalose | 50 | 5 | 75 |
| 42. Poloxamer 188 | Trehalose | 5 | 50 | 50 |
| 43. Trehalose | PEG 3350 | 50 | 5 | 41 |
| 44. Trehalose | PEG 3350 | 5 | 50 | 36 |

Table 5 shows the results of experiments with botulinum toxin formulations containing two non-protein excipients and with or without the specified buffer. The potency of the botulinum toxin was measured: (1) after lyophilization and immediate reconstitution ("Initial Potency"), and; (2) after lyophilization, storage for three months under one of two different storage conditions (at −40 degrees C. or at 20 degrees C.) and reconstitution.

The Table 5 results show that a botulinum toxin pharmaceutical composition containing a PVP non-protein excipient does not have significant room temperature stability unless formulated with a citrate buffer. I found that even at the same pH a phosphate buffer would not provide the desired room temperature stability for such a formulation.

TABLE 5

Botulinum Toxin Formulations with Two Non-Protein Excipients

| Non-Protein Excipients | Potency (Initial) | Potency (3 Month Freezer) | Potency (3 Month Room Temperature) |
|---|---|---|---|
| 20 mg sucrose 10 mg poloxamer | 101% | 117% | 87% |
| 20 mg sucrose 10 mg poloxamer 10 mM citrate (pH 5.5) | 77% | 81% | 81% |
| 20 mg sucrose 10 mg poloxamer 10 mM phosphate (pH 5.5) | 112% | 113% | 113% |
| 20 mg sucrose 10 mg poloxamer 10 mM citrate (pH 6.5) | 90% | Not obtained | 91% |
| 20 mg sucrose 10 mg poloxamer 10 mM phosphate (pH 6.5) | 95% | 119% | 88% |
| 20 mg PVP 10 mg poloxamer | 71% | 101% | <39% |
| 20 mg PVP 10 mg poloxamer 10 mM citrate (pH 5.5) | 65% | 101% | 65% |
| 20 mg PVP 10 mg poloxamer 10 mM phosphate (pH 5.5) | 71% | 79% | <39% |
| 20 mg PVP 10 mg poloxamer 10 mM citrate (pH 6.5) | 87% | 97% | <39% |
| 20 mg PVP 10 mg poloxamer 10 mM phosphate (pH 6.5) | 65% | 63% | <39% |

The Table 6 shows the results of experiments with botulinum toxin formulations containing three non-protein excipients and with or without the specified buffer. The potency of the botulinum toxin was measured after lyophilization followed by immediate reconstitution ("Initial Potency").

The Table 6 results show that a botulinum toxin pharmaceutical composition can be stabilized by use of three non-protein excipient present in the same formulation, and that the use of a citrate buffer in the formulation in the formulation improves initial potency. Botulinum toxin pharmaceutical compositions stabilized with other three different non-protein excipients, and with significant recovered potency, were also made.

TABLE 6

Botulinum Toxin Formulations with Three Non-Protein Excipients

| Non-Protein Excipients | Potency (Initial) |
|---|---|
| 20 mg sucrose 20 PVP 20 mg poloxamer | 67% |

TABLE 6-continued

Botulinum Toxin Formulations with Three Non-Protein Excipients

| Non-Protein Excipients | Potency (Initial) |
|---|---|
| 20 mg sucrose<br>20 mg PVP<br>20 mg poloxamer<br>10 mM citrate (pH 5.5) | 98% |

Among the discoveries made from these experiments were the following:

1. a botulinum toxin formulation prepared with particular to concentrations of a single non-protein excipient which is a polyvinylpyrrolidone (such as Kollidon 17) can show no recovered potency (see lines 1-4 of Table 1).

2. a botulinum toxin formulation prepared with different particular concentrations of a single non-protein excipient which is a polyvinylpyrrolidone (such as Kollidon 17) can show a recovered potency between 39% and 52% (see lines 1-3 of Table 2). In light of item 1. above this is a surprising and unexpected discovery.

3. a botulinum toxin formulation prepared with a two different non-protein excipients, wherein one of the non-protein excipients is a polyvinylpyrrolidone (such as Kollidon 17) can show no recovered potency (see lines 1-7 of Table 3).

4. a botulinum toxin formulation prepared with a two different non-protein excipients, wherein one of the non-protein excipients is a polyvinylpyrrolidone (such as Kollidon 17) can show a recovered potency as high as 65% (see lines 1-18 of Table 4). In light of items 1 and 3. above this is a surprising and unexpected discovery.

5. a botulinum toxin formulation prepared with a particular concentration of a single non-protein excipient which is a disaccharide (such as lactose) can show no recovered potency (see line 5 of Table 1).

6. a botulinum toxin formulation prepared with different particular concentrations of a single non-protein excipient which is a disaccharide (such as lactose) can show a recovered potency between 15% and 35% (see lines 4-5 of Table 2). In light of item 5. above this is a surprising and unexpected discovery.

7. a botulinum toxin formulation prepared with a two different non-protein excipients, wherein one of the non-protein excipients is a disaccharide (such as lactose) can show no recovered potency (see lines 1-3 of Table 3).

8. a botulinum toxin formulation prepared with a two different non-protein excipients, wherein one of the non-protein excipients is a is a disaccharide (such as lactose) can show a recovered potency as high as 65% (see lines 1-8 and 19-22 of Table 4). In light of items 5 and 7. above this is a surprising and unexpected discovery 9. a botulinum toxin formulation prepared with a single non-protein excipient which is a disaccharide (such as sucrose) can show no recovered potency (see lines 6-10 of Table 1).

10. a botulinum toxin formulation prepared with a two different non-protein excipients, wherein one of the non-protein excipients is a disaccharide (such as sucrose) can show no recovered potency (see lines 4-8, 11-12, and 19-27 of Table 3).

11. a botulinum toxin formulation prepared with two different non-protein excipients, wherein one of the non-protein excipients is a disaccharide (such as sucrose) can show a recovered potency as high as 59% (see lines 9-17, 20, 23, 26 and 30-35 of Table 4). In light of items 9. and 10 above this is a surprising and unexpected discovery.

12. a botulinum toxin formulation prepared with a single non-protein excipient which is an amino acid (such as glycine) can show no recovered potency (see lines 11-13 of Table 1).

13. a botulinum toxin formulation prepared with a two different non-protein excipients, wherein one of the non-protein excipients is a amino acid (such as glycine) can show no recovered potency (see lines 19-21, 28-30, 38, 42-44 and 46-48 of Table 3).

14. a botulinum toxin formulation prepared with different particular concentrations of two different non-protein excipients, wherein one of the non-protein excipients is an amino acid (such as glycine) can show a recovered potency as high as 33% (see lines 38-39 of Table 4). In light of items 12-13 above this is a surprising and unexpected discovery.

15. a botulinum toxin formulation prepared with a single non-protein excipient which is a metal (such as zinc) can show no recovered potency (see lines 14-16 of Table 1).

16. a botulinum toxin formulation prepared with a two different non-protein excipients, wherein one of the non-protein excipients is a metal (such as zinc) can show no recovered potency (see lines 8-9, 13-15, 22-24, and 28-37 of Table 3).

17. a botulinum toxin formulation prepared with different particular concentrations of two different non-protein excipients, wherein one of the non-protein excipients is a metal (such as zinc) can show a recovered potency as high as 38% (see lines 21 and 36-37 of Table 4). In light of items 15-16 above this is a surprising and unexpected discovery.

18. a botulinum toxin formulation prepared with a single non-protein excipient which is an alcohol (such as mannitol) can show no recovered potency (see lines 17-19 of Table 1).

19. a botulinum toxin formulation prepared with a two different non-protein excipients, wherein one of the non-protein excipients is an alcohol (such as mannitol) can show no recovered potency (see lines 9-18 of Table 3).

20. a botulinum toxin formulation prepared with different particular concentrations of two different non-protein excipients, wherein one of the non-protein excipients is an alcohol (such mannitol) can show a recovered potency as high as 35% (see lines 22-29 of Table 4). In light of items 17-18 above this is a surprising and unexpected discovery.

21. a botulinum toxin formulation prepared with a single non-protein excipient which is a disaccharide (such as trehalose) can show no recovered potency (see lines 23-25 of Table 1).

22. a botulinum toxin formulation prepared with a two different non-protein excipients, wherein one of the non-protein excipients is a disaccharide (such as trehalose) can show no recovered potency (see lines 16-18, 25-27, 33-35 and 42-45 of Table 3).

23. a botulinum toxin formulation prepared with different particular concentrations of two different non-protein excipients, wherein one of the non-protein excipients is a disaccharide (such as trehalose) can show a recovered potency as high as 75% (see lines 40-44 of Table 4). In light of items 21-22 above this is a surprising and unexpected discovery.

24. a botulinum toxin formulation prepared with a single non-protein excipient which is a polyethylene glycol (such as PEG 3350 or poloxamer 188) can show no recovered potency (see lines 29-30 of Table 1).

25. a botulinum toxin formulation prepared with a two different non-protein excipients, wherein one of the non-protein excipients is a polyethylene glycol (such as PEG 3350 or poloxamer 188) can show no recovered potency (see lines 10, 31-32, 36-41 and 45-48 of Table 3).

26. a botulinum toxin formulation prepared with different particular concentrations of two different non-protein excipients, wherein one of the non-protein excipients is a polyethylene glycol (such as PEG 3350 or poloxamer 188) can show a recovered potency as high as 75% (see lines 18-19, 24-25, 27-44 of Table 4). In light of items 24-25 above this is a surprising and unexpected discovery.

27. The non-protein stabilizers lactose and polyvinylpyrrolidone ("PVP") (i.e. Kollidon 17) each provided significant recovery potency when used as a non-protein stabilizer of the botulinum toxin present in a botulinum toxin pharmaceutical composition (see Table 2).

28. When lactose and PVP used were both used as non-protein stabilizers of the same botulinum toxin pharmaceutical composition the recovery potency improved, as compared to the recovery potency observed when the lactose and PVP where used separately as a non-protein stabilizer (see eg Table 4, lines 1-8).

29. Recovery potency (of the botulinum toxin present in a reconstituted botulinum toxin pharmaceutical composition) improved when lactose and/or PVP were used with one or more of the other non-protein excipients set forth above (see, respectively, Table 4, lines 19-22, and Table 4, lines 9-18).

30. Use of certain combinations of excipients (as non-protein stabilizers of the botulinum toxin present in a reconstituted botulinum toxin pharmaceutical composition) provided a significant recovery potency even where no recovery potency was obtained when either such nonprotein excipient was used by itself as a non-protein stabilizer of the botulinum toxin present in a botulinum toxin pharmaceutical composition. For example, compare: (1) Table 1, lines 1-4 and Table 1, lines 6-10, with Table 4, lines 9-17, and; (2) Table 1, line 23-25 and Table 1, line 29, with Table 4, 43-44.

31. Recovery potency was sometimes dependent upon the concentration of the non-protein stabilizer present in the botulinum toxin pharmaceutical composition 32. Addition of a buffer could improve recovery potency and storage stability. Individual buffers differed in their capacity to exert this effect. The buffers act to obtain optimal pH, maintain optimal pH, and in some instances (e.g., citrate) to protect against oxidation.

General conclusions from these experiments include the observations that:

(a) The botulinum toxin present in a botulinum toxin pharmaceutical composition can be stabilized (and shown by a good recovery potency) by formulating the composition with two or more common non-protein excipients.

(b) a polyvinylpyrrolidone (such as Kollidon 17) and a disaccharide (such as lactose) can function as a non-protein stabilizer (excipient) in a botulinum toxin formulation without the presence of any other non-protein stabilizer.

(c) with the same non-protein stabilizer or stabilizers, recovered potency can be dependent upon the ratio of and/or the concentration of the non-protein stabilizer or stabilizers used in the botulinum toxin formulation.

(d) certain non-protein stabilizers (such as a polyvinylpyrrolidone [such as Kollidon 17] and a disaccharide [such as lactose]) not only can act to stabilize the botulinum toxin in a botulinum toxin formulation when used together, but can provide an enhanced stabilization when used together, as determined by a higher recovered potency of the reconstituted formulation.

(e) commonly used pharmaceutical excipients (such as polyvinylpyrrolidone, lactose, sucrose etc) did not function when used as stabilizers, or only function as a stabilizer of a botulinum toxin in a non-protein botulinum toxin formulation when used at particular concentrations. a polyvinylpyrrolidone (such as Kollidon 17) and a disaccharide (such as lactose)

(f) Many excipients functioned or functioned as better stabilizers of a botulinum toxin in a non-protein botulinum toxin formulation when combined with a polyvinylpyrrolidone (such as Kollidon 17) or with a disaccharide (such as lactose).

(g) Although the specific PVP "Kollidon 17" was used in &number of the botulinum toxin formulations made other PVPs are within the scope of the present invention.

(h) Although the specific poloxamer "polyoxamer 188" was used in a number of the botulinum toxin formulations made other poloxamers are within the scope of the present invention.

(i) It was found that the surfactant polysorbate (Tween) can be used instead of poloxamer 188 with similar results.

Other non-protein excipients which can be used in a botulinum toxin pharmaceutical composition within the scope of the present invention include antioxidants such as butylated Hydroxytoluene (BHT) and butylated Hydroxyanisole (BHA) and amino acids such as cysteine and methionine. The lyophilized botulinum toxin formulation can be reconstituted with saline, water or with a custom diluent to affect the performance after reconstitution or injection.

Example 3

Use of a Botulinum Toxin Pharmaceutical Composition

A 48 year old male is diagnosed with a spastic muscle condition, such as cervical dystonia. Between about $10^{-3}$ U/kg and about 35 U/kg of a botulinum toxin type A pharmaceutical composition of formulation containing lactose and PVP is injected intramuscularly into the patient. Within 1-7 days the symptoms of the spastic muscle condition are alleviated and alleviation of the symptoms persists for at least from about 2 months to about 6 months.

A pharmaceutical composition according to the invention disclosed herein has many advantages, including the following:

1. the pharmaceutical composition can be prepared free of any blood product, such as albumin and therefore free of any blood product infectious element such as a prion.

2. the pharmaceutical composition has stability and high % recovery of toxin potency comparable to or superior to that achieved with currently available pharmaceutical compositions.

3. reduced toxicity, as assessed by either intramuscular or intravenous administration.

4. reduced antigenicity.

Various publications, patents and/or references have been cited herein, the contents of which, in their entireties, are incorporated herein by reference.

Although the present invention has been described in detail with regard to certain preferred methods, other embodiments, versions, and modifications within the scope of the present invention are possible. For example, a wide variety of stabilizing polysaccharides and amino acids are within the scope of the present invention.

Accordingly, the spirit and scope of the following claims should not be limited to the descriptions of the preferred embodiments set forth above.

I claim:

1. A pharmaceutical composition comprising:
   (a) a botulinum toxin,
   (b) about 5 mg to about 20 mg of a polyvinylpyrrolidone for each about 100 units of the botulinum toxin, and
   (c) about 0.5 mg to about 250 mg of lactose,
   wherein the potency of the botulinum toxin is at least about 40% to about 50% of the theoretical maximum potency of the botulinum toxin.

2. The pharmaceutical composition of claim 1, wherein the botulinum toxin is a biologically active botulinum toxin.

3. The pharmaceutical composition of claim 1, wherein the botulinum toxin is selected from the group consisting of the botulinum toxins types A, B, C, D, E, F and G.

4. The pharmaceutical composition of claim 1, wherein the botulinum toxin is a botulinum toxin type A.

5. The pharmaceutical composition of claim 1, wherein a function of the polyvinylpyrrolidone is to stabilize the botulinum toxin.

6. A pharmaceutical composition comprising:
   (a) a botulinum toxin,
   (b) about 5 mg of a polyvinylpyrrolidone for each about 100 units of the botulinum toxin, and
   (c) about 5 mg of lactose,
   wherein the potency of the botulinum toxin is at least about 50% of the theoretical maximum potency of the botulinum toxin.

7. A pharmaceutical composition comprising:
   (a) a botulinum toxin, wherein the botulinum toxin is not stabilized by a protein excipient,
   (b) about 20 mg of a polyvinylpyrrolidone for each about 100 units of the botulinum toxin, and
   (c) about 5 mg to about 250 mg of lactose,
   wherein the potency of the botulinum toxin is at least about 40% of the theoretical maximum potency of the botulinum toxin.

8. The pharmaceutical composition of claim 7, wherein the botulinum toxin is a biologically active botulinum toxin.

9. The pharmaceutical composition of claim 7, wherein the botulinum toxin is selected from the group consisting of the botulinum toxins types A, B, C, D, E, F and G.

10. The pharmaceutical composition of claim 7, wherein the botulinum toxin is a botulinum toxin type A.

11. The pharmaceutical composition of claim 7, wherein a function of the polyvinylpyrrolidone is to stabilize the botulinum toxin.

12. A pharmaceutical composition comprising:
    (a) a botulinum toxin, wherein the botulinum toxin is not stabilized by a protein excipient,
    (b) about 10 mg of a polyvinylpyrrolidone for each about 100 units of the botulinum toxin, and
    (c) about 0.5 mg to about 250 mg of lactose,
    wherein the potency of the botulinum toxin is at least about 50% of the theoretical maximum potency of the botulinum toxin.

* * * * *

UNITED STATES PATENT AND TRADEMARK OFFICE
CERTIFICATE OF CORRECTION

| | | |
|---|---|---|
| PATENT NO. | : 8,137,677 B2 | |
| APPLICATION NO. | : 11/524683 | |
| DATED | : March 20, 2012 | |
| INVENTOR(S) | : Terrence J. Hunt | |

It is certified that error appears in the above-identified patent and that said Letters Patent is hereby corrected as shown below:

On Title page, in field (60), under "Related U.S. Application Data", in column 1, line 1, Delete "60/725,426," and insert -- 60/725,126, --, therefor.

On Title page, in field (56), under "OTHER PUBLICATIONS", in column 2, line 14, Delete "botulinal" and insert -- botulinum --, therefor.

On Title page, in field (56), under "OTHER PUBLICATIONS", in column 2, line 20, Delete "(R))" and insert -- ®) --, therefor.

On Title page, in field (57), under "ABSTRACT", in column 2, line 5, Delete "disaccharides," and insert -- disaccharide, --, therefor.

In column 3, line 8, Delete "present," and insert -- present --, therefor.

In column 7, line 22, Delete "botulinal" and insert -- botulinum --, therefor.

In column 7, line 35, Before "Available" insert -- 1 --.

In column 7, line 35, Delete "Irving," and insert -- Irvine, --, therefor.

In column 7, line 55, Delete "sublimus:" and insert -- sublimis: --, therefor.

In column 12, line 8, Delete "free" and insert -- free" --, therefor.

In column 13, line 66, Delete "toxins," and insert -- toxins --, therefor.

In column 14, line 38, Before "polyvinylpyrrolidone" delete "to".

In column 15, line 17, After "toxin" insert -- is --.

Signed and Sealed this
Fifth Day of June, 2012

David J. Kappos
*Director of the United States Patent and Trademark Office*

CERTIFICATE OF CORRECTION (continued)
U.S. Pat. No. 8,137,677 B2

In column 23, line 14, Before "concentrations" delete "to".

In column 23, line 52, after "discovery" insert -- . --.

In column 25, line 37, After "composition" insert -- . --.

In column 26, line 1, Delete "concentrations." and insert -- concentrations, --, therefor.

In column 26, line 3, After "lactose)" insert -- . --.

In column 26, line 10, Delete "&number" and insert -- a number --, therefor.

In column 26, line 12, Delete ""polyoxamer" and insert -- "poloxamer --, therefor.